US00PP33091P3

(12) United States Plant Patent
Shipley

(10) Patent No.: US PP33,091 P3
(45) Date of Patent: May 25, 2021

(54) DESERT WILLOW TREE NAMED 'SWEET BUBBA'

(50) Latin Name: *Chilopsis linearis*
Varietal Denomination: Sweet Bubba

(71) Applicant: Nicholas Benoit Shipley, Tucson, AZ (US)

(72) Inventor: Nicholas Benoit Shipley, Tucson, AZ (US)

( * ) Notice: Subject to any disclaimer, the term of this patent is extended or adjusted under 35 U.S.C. 154(b) by 0 days.

(21) Appl. No.: 16/602,100

(22) Filed: Aug. 7, 2019

(65) Prior Publication Data

US 2021/0045272 P1 Feb. 11, 2021

(51) Int. Cl.
*A01H 5/02* (2018.01)
*A01H 6/00* (2018.01)

(52) U.S. Cl.
USPC ..... Plt./216
CPC ..... *A01H 6/00* (2018.05); *A01H 5/02* (2013.01)

(58) Field of Classification Search
USPC ..... Plt./216, 226
CPC ..... A01H 5/02; A01H 5/00; A01H 6/00
See application file for complete search history.

(56) References Cited

U.S. PATENT DOCUMENTS

PP11,078 P * 10/1999 Mathews ..... Plt./216
PP28,902 P3 * 1/2018 Gass ..... Plt./216

OTHER PUBLICATIONS

Henrickson A Taxonomic Revision of *Chilopsis* (Bignoniaceae) Aliso: A Journal of Systematic and Evolutionary Botany 11(2), Article 7, 1985 179-197. (Year: 1985).*
Issuu ACLA Mar./Apr. 2019 Civano Growers: Pioneering Plants that Beautify the Southwest, retrieved on Mar. 25, 2019, retrieved from the Internet at https://issuu.com/aosinc/docs/acla_marapr19, cover page, p. 12. (Year: 2019).*

* cited by examiner

*Primary Examiner* — June Hwu

(57) ABSTRACT

A new and distinct *Chilopsis linearis* tree named Sweet Bubba is characterized by an upright form, fast growth, dark green leaves and having flowers with crisped corollas with a distinctive red/purple color (70A, R.H.S. color chart) and blooming throughout the warm season (locally May-October). No seed production has been noted, beneficial for more flowering and less trash in the landscape.

4 Drawing Sheets

Latin name: *Chilopsis linearis*.
Varietal denomination: Sweet Bubba.

INTRODUCTION

*Chilopsis linearis*, commonly known as desert willow, is a large shrub or up to a medium, typically multitrunked tree, occasionally reaching 25 feet tall×40 feet wide in favorable locations such as broad washes. Trunk diameters can reach 2-3 feet in diameter, although trees this large are rare. Desert willow grows wild throughout much of the arid and semiarid southwestern United States and northern Mexico up to an elevation of about 6000'. *Chilopsis* stands are most commonly found adjacent to and within normally dry washes. Desert willow has been successfully utilized as a small-medium sized landscape tree throughout much of the southwestern US, tolerating extreme heat combined with low water use. *Chilopsis* is rarely freeze damaged within its region of cultivation. The trees have large trumpet shaped flowers generally produced throughout the warm season as long as moisture is available. Flower color ranges from white to pink to a deep magenta or maroon, depending on the seed source or cultivar. Both large bees and hummingbirds visit the flowers for nectar. A variety of cultivars, some patented, as well as seedling forms are available in the trade.

BACKGROUND OF THE INVENTION

The present invention relates to a new and distinct cultivar of *Chilopsis linearis*. The cultivar originated from a cross between *Chilopsis linearis* 'Sweet Katie Burgundy' and *Chilopsis linearis* 'Bubba' with 'Sweet Katie Burgundy' as the female parent. *Chilopsis linearis* 'Sweet Bubba' is a selection from the $F_1$ generation of that cross and is the object of this application.

SUMMARY OF THE INVENTION

Among the features that distinguish the new *Chilopsis* cultivar from all other available and commercial varieties of *Chilopsis* known to the inventor are the following combination of characteristics: upright form, blooms produced throughout the warm season (locally May-October), fast growth, dark green leaves, seedlessness, and crisped corollas with a distinctive red/purple color (70A, R.H.S. color chart).

The propagation procedure is as follows: Four inch long semi-hardwood cuttings have the lower leaves removed, and then soaked in 5:1 DIP'N GROW™. Cuttings are placed in peat media in grow trays, then moved to a fog propagation house near Sahuarita, Ariz. where they are misted every 30 minutes with the soil temperature maintained between 75-85° F. Rooting is essentially complete within 4 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Chilopsis linearis* 'Sweet Bubba' growing near Sahuarita, Ariz., depicted in color as nearly correct as it is possible to make in a color illustration of the character.

DETAILED PLANT DESCRIPTION

Figure 1:
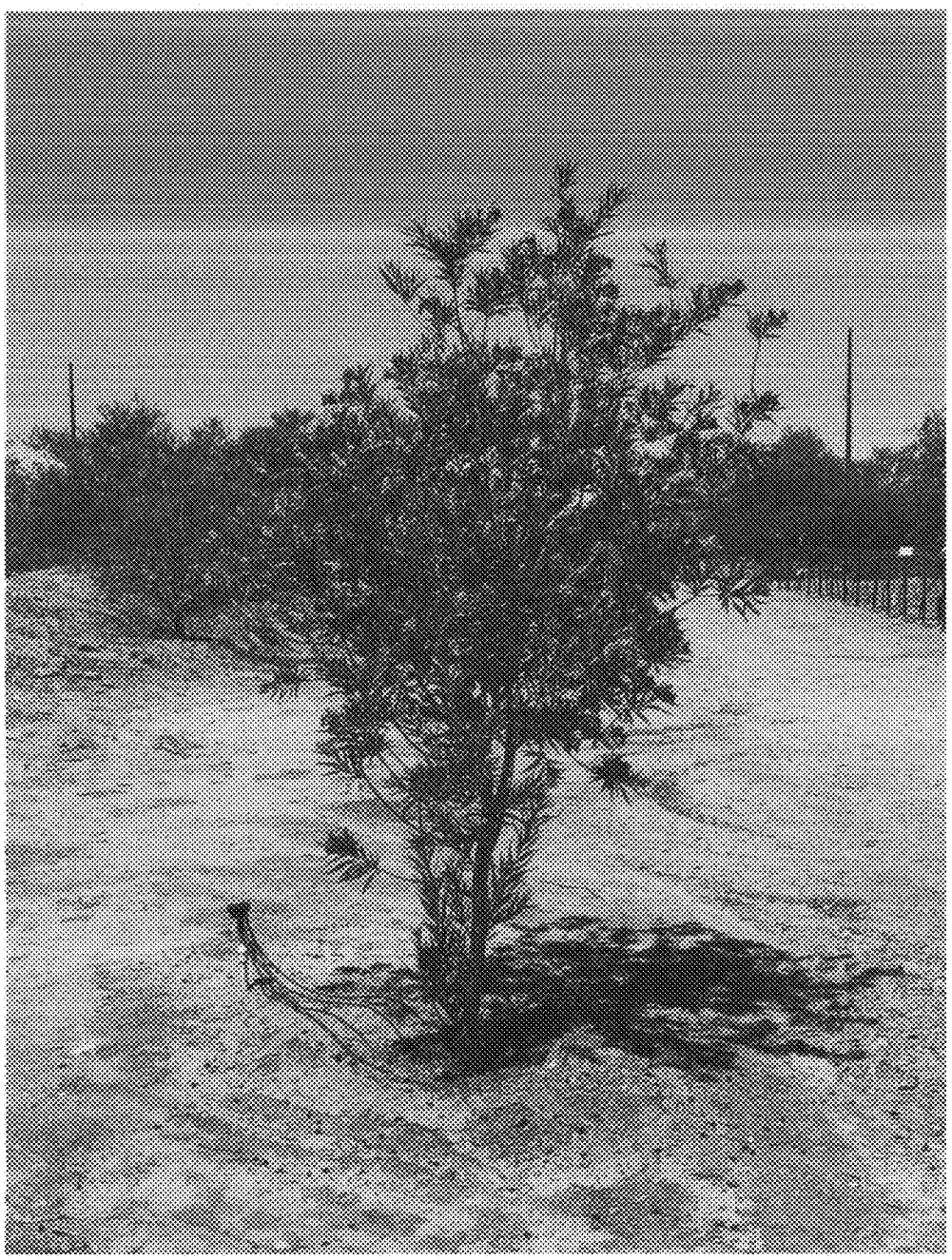
FIG. 1 shows *Chilopsis linearis* 'Sweet Bubba' at age 6 years growing at a commercial nursery near Sahuarita, Ariz.
Figure 2:
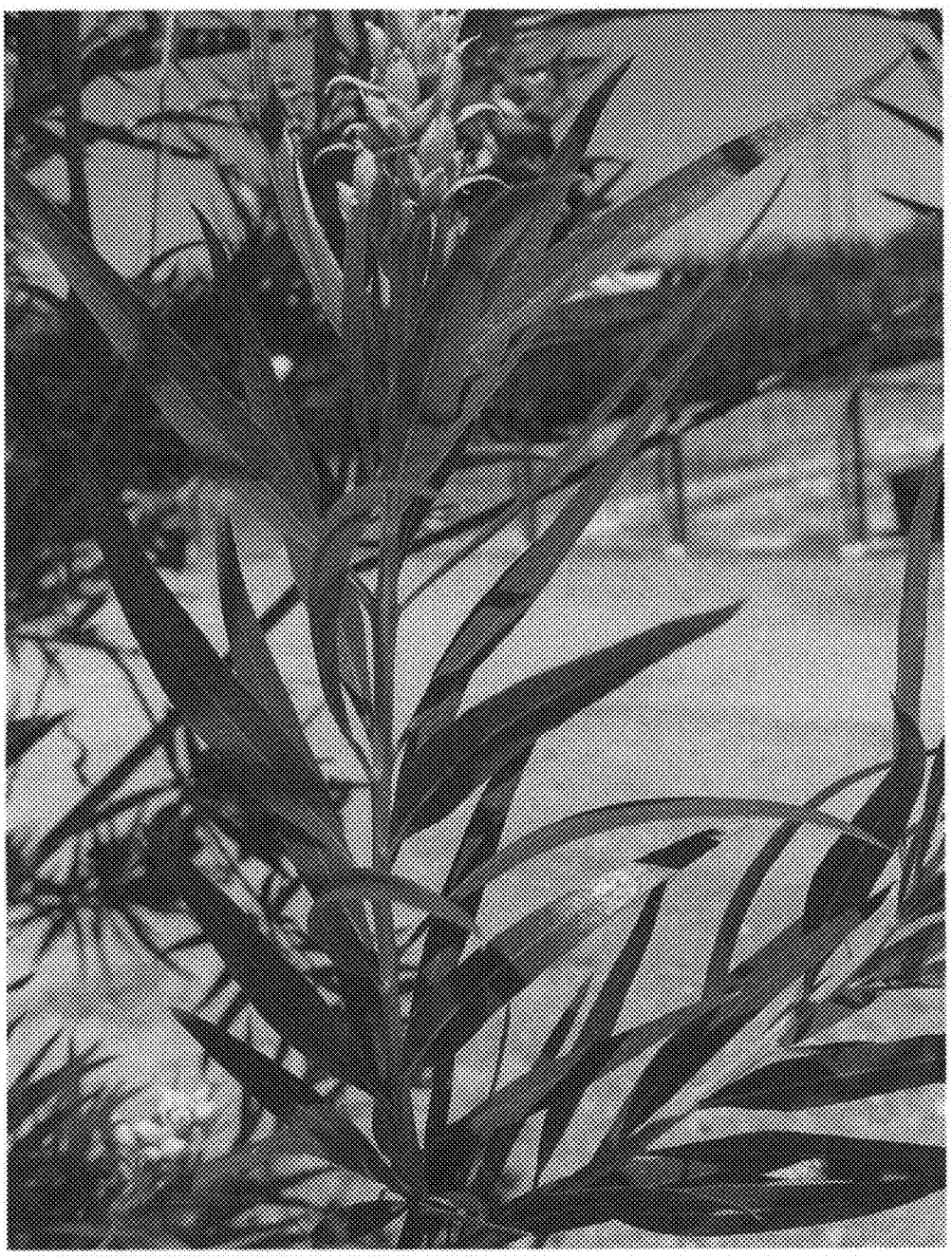
FIG. 2 shows the young leaves and young stem of *Chilopsis linearis* 'Sweet Bubba'.
Figure 3:
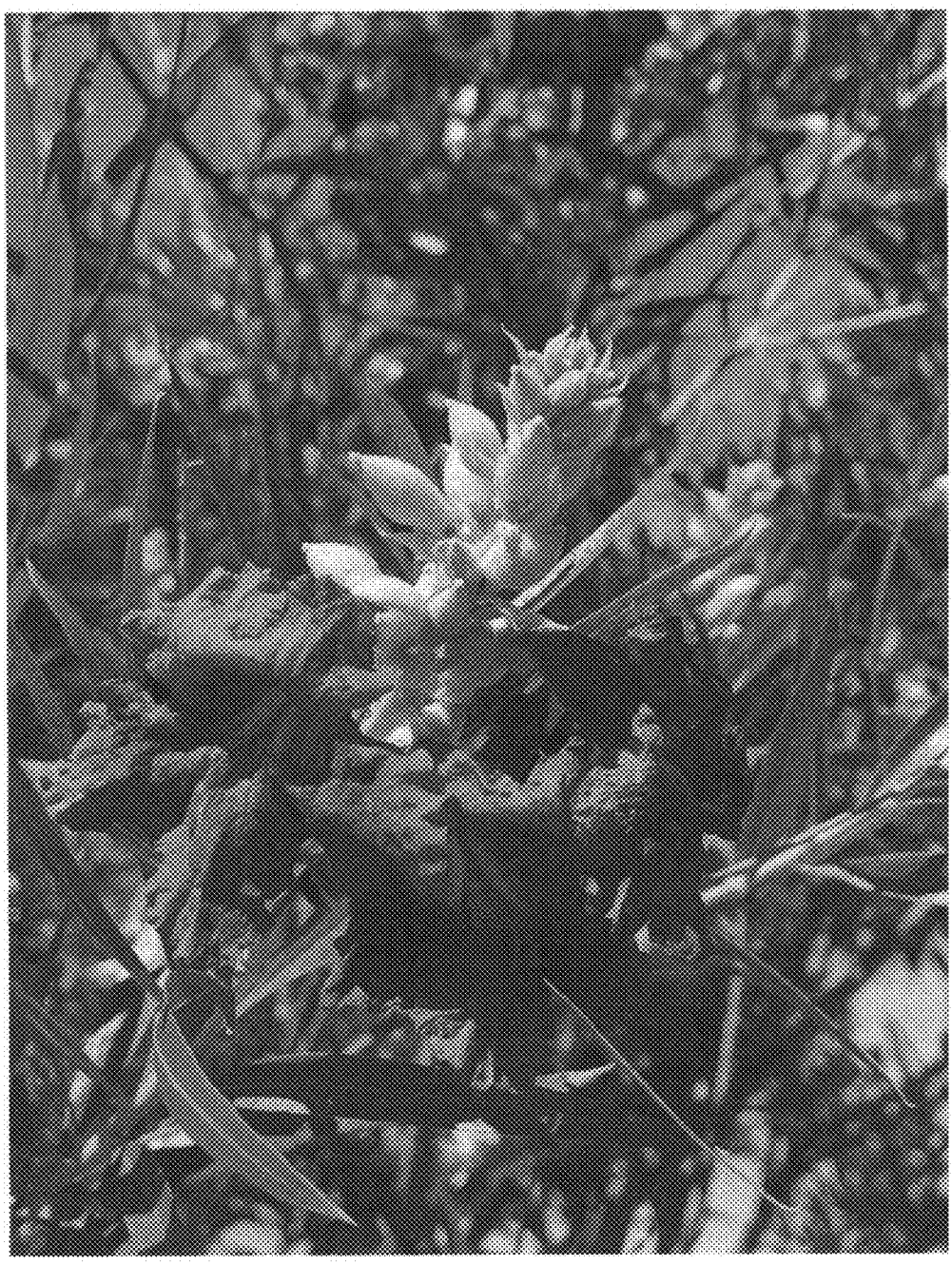
FIG. 3 shows the flowers and inflorescence of *Chilopsis linearis* 'Sweet Bubba'.
Figure 4:
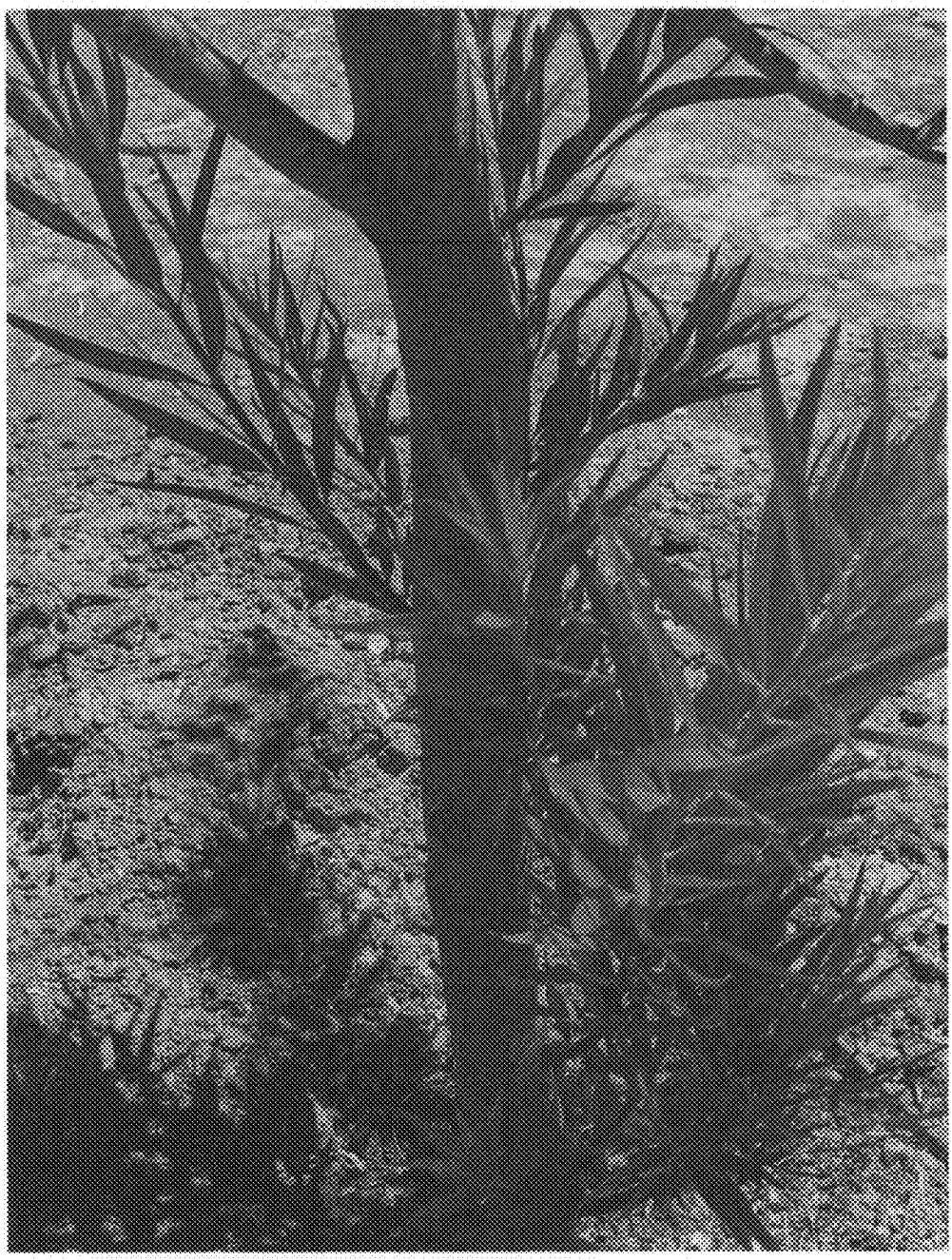
FIG. 4 shows the older branches and trunk of *Chilopsis linearis* 'Sweet Bubba'.

The following is a detailed description of the new desert willow tree based upon examination and measurements of the original specimen at age 6 years growing in a commercial plant nursery near Sahuarita, Ariz. The color descriptions are based upon the 5th edition R.H.S. Colour Chart, 2007. Color names other than common usage are as listed in *COLOR Universal Language and Dictionary of Names,* by Kenneth L. Kelly and Deane B. Judd; National Bureau of Standards special publication 440. Washington, D.C. :U.S. Department of Commerce, National Bureau of Standards, December 1976.

The 'Sweet Bubba' specimen at age 6 years is a small multitrunked tree about 10 feet tall×7 feet wide. Trunk caliper at this age measures 2.5-3.0". Branch angle varies from 30-60°. Bark at this age is still relatively smooth and has not yet developed the rough and cracked surface typical of this tree at maturity. Color on oldest mature sterns measuring from 2-70 mm in diameter varies from N1876-D.

Bark on older maturing, terete stems measure 2.5-3.5 mm in diameter is colored 187A. Scattered lenticels are present measuring 0.25-1.0 mm long×0.08-0.33 mm wide, color 199A. Maturing young stems are colored 145B with an admixture of 185B on the sunward side. Lenticels are scattered at this age measure 0.25-1.0 mm long×0.08-0.33 mm wide, colored 185B at this stage of growth.

Young, growing stems measure 2-2.5 mm in diameter and are irregularly angular in cross section. Color is 144B. Stems at this stage are covered with very fine ascending straight hairs, these caducous by maturity.

Leaves are mostly alternate, lanceolate, acute both apically and basally, sessile with a basal pulvinus, glabrous, glossy (sub viscid) on both surfaces. Abaxial leaf surface has slightly raised veins, the veins colored 193A, reticulate. Adaxial veins less prominent, colored 138B. Both leaf surfaces colored alike, N137A on mature leaves. Mature leaves measure 25-120 mm long×5-15 mm wide. Young, growing leaves are colored closest to 144A.

Leaf pulvinus is horizontally elliptical in cross section, measuring 1.3-2.0 mm long×1.25 mm high×1.5 mm wide colored 193A on mature leaves.

Axillary buds are inconspicuous to invisible, measuring less than 0.5 mm colored 138B when visible.

Inflorescence is a reduced panicle, which on superficial examination appears to be a raceme. Inflorescence measures up to 17 cm long×9-10 cm wide. Inflorescence axis measures 2 mm in diameter basally tapering to 1 mm in diameter apically. Mature inflorescence axis colored 199C. Buds are more or less obovoid, 8-12 mm long×4-8 mm in diameter just before anthesis. A small rounded knob (1 mm diameter) is visible at the apex of the flower bud. Bud surface tomentulose, the hairs thinning before anthesis. Bud color close to 149A on young buds, changing to N155C mottled with 75A just before anthesis.

Flower bracts measure 3-3.6 mm long×0.7-1.1 mm wide, more or less lanceolate in shape. Abaxial surface is tomentulose, adaxial surface glabrous. Bracts paired, located near the midpoint of the pedicel, which measures 4-8 mm long× 1-1.25 mm diameter. Pedicel color is 70A above the bract attachment, 142D below. Pedicels are tomentulose, the hairs caducous near anthesis. Bract color is close to 149B, fading to 149D before falling away. Bracts are caducous before anthesis. Flower measures 38-46 mm long×28 mm high×28 mm wide, trumpet shaped, comprised of 5 mostly fused petals, the tube descending at the calyx then flaring unequally at the limb, the lower 3 corolla lobes extending further than the upper 2. Corolla mostly colored 70A. Flowers last about 2 days. The corolla is deciduous at the floral disc.

Flowers have a pleasant, but subtle sweet smell.

The floral disc (receptacle) is nectiferous, 1 mm long×2 mm wide, discoid, colored 154D except 70A immediately adjacent to the calyx.

Calyx of 5 more or less fused sepals, totally enclosing the other floral parts in bud, appearing bilabiate at anthesis, opening on the lateral edges about ⅓-½ the length from the apex. Calyx color close to 149A on young buds, changing to N155C mottled with 75A just before anthesis. Calyx covered with tomentulose hairs abaxially, glabrous adaxially, the hairs mostly caducous at or soon after anthesis.

Corolla crisped, mostly glabrous, colored mostly 70A except on the ventral portion of the tube, where color 71B alternates with and is mottled into 2 main longitudinal bands of 20A, these bands most prominently displayed on 2 longitudinal ridges where scattered, uncolored, crooked hairs 1-2 mm in length can be seen. The ridges diverge from the corolla base toward the limb. The ridges measure about 3 mm high×2 mm wide, these seen as indentations when viewed from the flower exterior. Guidelines, colored 71 B are also present on the ventral portion of the corolla, these spreading gradually with the corolla flare. The area between the guidelines and not on the ridges is mottled with color 68C. The outer lower throat is colored much like the adjacent interior area.

Flowers have 4 epipetalous stamens and one staminode, the stamens of 2 lengths, the upper 2 shorter than the lower 2. The staminode attachment is located between the upper stamens. Long stamens are 27-30 mm long, while the short stamens measure 23-25 mm long. Filaments measure about 1 mm diameter at the base tapering to about 0.5 mm just below the anthers. Filaments are colored 157B. Anthers basifixed, explanate to somewhat reflexed, measuring 2.5 mm long×1.5 -2 mm wide. Anthers and pollen colored 155C. Staminode measures 17 mm long×0.5 mm diameter, color 157B.

The pistil is single, comprised of 2 carpels. Pistil measures 26 mm long. Ovary measures 3 mm long×1.5 mm wide, oblongoid in shape, color 154D. Style measures 20 mm long×0.5 mm diameter, terete, somewhat flattened laterally near the stigma, color 157B. Stigma measures 3 mm long×1.5 mm wide×0.2 mm thick when closed, slightly obovate, color 157B. Stigma is doubled and flaring at anthesis, sensitive, closing when touched.

Fruit and seeds: the fruit of *Chilopsis linearis* is a many-seeded silique. 'Sweet Bubba' is apparently sterile, at least under the growing conditions present in Sahuarita, Ariz., as no fruits were seen throughout the 2018 growing season. Other cultivars of *Chilopsis* produced from few to many fruits under identical growing conditions.

Based upon the elevational range of the species, 'Sweet Bubba' should be hardy to at least USDA cold hardiness zone 7 and has been planted successfully in Phoenix, Ariz. where high temperatures can exceed 120° F.

No disease or insect problems were noted on the examined plants and have not been seen at the nursery near Sahuarita, Ariz.

COMPARISONS TO RELATED *CHILOPSIS*

Compared to its maternal parent, 'Sweet Katie Burgundy', 'Sweet Bubba' is faster growing, as well as larger and more upright in growth form, has a calyx much lighter in color, and a lighter colored, more crisped corolla and is seedless compared to few fruited in its maternal parent. Compared to its paternal parent, 'Bubba', 'Sweet Bubba' has a flower of relatively uniform color, while 'Bubba' has two-toned flowers, pink over burgundy. Growth rate for 'Sweet Bubba' and 'Bubba' are similarly fast. 'Bubba' is few fruited compared to 'Sweet Bubba' with no fruits.

Corollas of 'Sweet Bubba' are more crisped than those of 'Bubba'. Calyx of 'Bubba' and 'Sweet Bubba' are similarly light in color.

There are numerous named and a couple of patented cultivars of *Chilopsis linearis*. Many of the named cultivars have gone out of cultivation and those will not be discussed. The majority of the remaining cultivars can easily be distinguished by flower color, vigor, and growth form. Other useful characters will be included if helpful for distinguishing the cultivars.

The following cultivars may be separated on the basis of flower color alone:

'Paradise' has pink flowers. 'Tejas' has pink to reddish purple flowers. 'Art's Seedless' has pink over burgundy flowers. 'Warren Jones' has pink, crisped flowers. 'AZT Bi-color' has pink over maroon flowers. 'AZT Dora's Desert Rose' has pink flowers. 'Barranco' has pink over maroon flowers. 'Hope' has white flowers with a yellow throat. 'Regal' has lavender over wine red flowers. 'Monhews' (U.S. Plant Pat. No. 11,078 P) is the same plant as 'Timeless Beauty' and has lavender over burgundy flowers. 'White Storm' has white flowers. 'Alpine' has large, pink flowers. 'Burgundy' is the same plant as 'Burgundy Lace' and has white-pink over pink-magenta flowers. 'Dark Storm' has lavender over wine red flowers. 'Lois Adams' has pale lavender over magenta flowers. 'Marfa Lace' has semi-double flowers colored pink over rose. 'Mesquite Valley Pink' is the same plant as 'Pink Star', which has ruffled dark pink flowers with a yellow throat.

Cultivars 'Rio Salado' and 'AZT Amethyst' have flowers somewhat similar to 'Sweet Bubba', but both cultivars produce fruits and seeds, while 'Sweet Bubba' is seedless. 'Lucretia Hamilton' has bicolored flowers with wine over maroon and also produces reduced amounts of fruits.

'MSWNLopur' (U.S. Plant Pat. No. 28,902 P3) has a different flower color N79A-B compared to 'Sweet Bubba' color 70A. 'MSWNLopur' also differs from 'Sweet Bubba' in leaf color, 146A-B for 'MSWNLopur' compared to N137A for 'Sweet Bubba'. Additionally, 'MSWNLopur' is reported to have opposite leaves while the leaves of 'Sweet Bubba' are mostly alternate.

I claim:

1. A new and distinct *Chilopsis linearis* tree substantially as described and illustrated herein.

* * * * *